(12) United States Patent
Ji et al.

(10) Patent No.: US 9,408,990 B2
(45) Date of Patent: Aug. 9, 2016

(54) OXYGEN MIXING VALVE

(71) Applicant: Beijing Aeonmed Co., Ltd., Beijing (CN)

(72) Inventors: Jinquan Ji, Beijing (CN); Jun Wang, Beijing (CN)

(73) Assignee: Beijing Aeonmed Co., Ltd., Beijing (CN)

( * ) Notice: Subject to any disclaimer, the term of this patent is extended or adjusted under 35 U.S.C. 154(b) by 356 days.

(21) Appl. No.: 13/985,817

(22) PCT Filed: Dec. 25, 2012

(86) PCT No.: PCT/CN2012/087405
§ 371 (c)(1),
(2) Date: Oct. 9, 2013

(87) PCT Pub. No.: WO2013/097701
PCT Pub. Date: Jul. 4, 2013

(65) Prior Publication Data
US 2014/0069431 A1    Mar. 13, 2014

(30) Foreign Application Priority Data

Dec. 30, 2011 (CN) .......................... 2011 1 0457730

(51) Int. Cl.
*A61M 16/12* (2006.01)
*A61M 16/20* (2006.01)
(Continued)

(52) U.S. Cl.
CPC ........... *A61M 16/0057* (2013.01); *A61M 16/12* (2013.01); *A61M 16/20* (2013.01);*B01F 3/02* (2013.01); *B01F 5/008* (2013.01); *F16K 11/048* (2013.01); *F16K 31/52416* (2013.01); *F16K 31/52425* (2013.01);
(Continued)

(58) Field of Classification Search
CPC . G05D 11/132; B01F 5/008; F16K 31/52425; F16K 11/048; A61M 16/20; A61M 2039/226; A61M 2039/248; A61M 2202/0208
See application file for complete search history.

(56) References Cited

U.S. PATENT DOCUMENTS 3,028,860 A * 4/1962 Gagnan ............... B63C 11/2209
                                                                128/202.22
4,072,148 A    2/1978 Munson et al.
(Continued)

FOREIGN PATENT DOCUMENTS

CN    101310790 A    11/2008
CN    101757713 A    6/2010
(Continued)

OTHER PUBLICATIONS

International Search Report issued in International Application No. PCT/CN2012/087405 dated Mar. 28, 2013.

*Primary Examiner* — Kevin Murphy
*Assistant Examiner* — Patrick Williams
(74) *Attorney, Agent, or Firm* — Venable LLP; Henry J. Daley (57) ABSTRACT

An oxygen mixing valve comprises a valve body. The valve body has an oxygen inlet, an air inlet, and a gas mixture outlet. A mixing chamber in communication with the gas mixture outlet, an oxygen chamber in communication with the oxygen inlet, and an air chamber in communication with the air inlet are disposed in the valve body. A first guide seat is elastically disposed in the oxygen chamber, and a second guide seat is elastically disposed in the air chamber. A first ball and a second ball are respectively disposed at inner ends of the first guide seat and the second guide seat. The first ball and the second ball are connected through a ball mandril. A mandril is movably disposed at an outer end of the first guide seat, a bearing capable of rotating is disposed at an outer side of the mandril, an involute cam is disposed at an outer side of the bearing, and the involute cam is connected to an output shaft of a stepper motor. The oxygen mixing valve has advantages of simple structure, convenient mounting and maintenance, low manufacturing cost, capability of sensitively and precisely adjusting the ratio of the oxygen to air, and capability of controlling the tidal volume in conjunction with a common proportional valve.

13 Claims, 7 Drawing Sheets

(51) Int. Cl.
*F16K 11/048* (2006.01)
*B01F 3/02* (2006.01)
*A61M 16/00* (2006.01)
*F16K 31/524* (2006.01)
*B01F 5/00* (2006.01)
*G05D 11/13* (2006.01)
*A61M 39/22* (2006.01)
*A61M 39/24* (2006.01)

(52) U.S. Cl.
CPC ............ *G05D 11/132* (2013.01); *A61M 16/122* (2014.02); *A61M 2039/226* (2013.01); *A61M 2039/248* (2013.01); *A61M 2202/0208* (2013.01)

(56) References Cited

U.S. PATENT DOCUMENTS

| | | | |
|---|---|---|---|
| 4,195,817 A | * | 4/1980 | Cramer .................. A62B 9/022 137/508 |
| 4,527,557 A | | 7/1985 | DeVries et al. |
| 5,433,385 A | | 7/1995 | Sakagami et al. |

FOREIGN PATENT DOCUMENTS

| | | |
|---|---|---|
| CN | 201612919 U | 10/2010 |
| CN | 102114296 A | 7/2011 |
| RU | 2103564 C1 * | 1/1998 |

* cited by examiner

| number of steps of motor | oxygen concentration in mixing cavity | number of steps of motor | oxygen concentration in mixing cavity | number of steps of motor | oxygen concentration in mixing cavity | number of steps of motor | oxygen concentration in mixing cavity | number of steps of motor | oxygen concentration in mixing cavity | number of steps of motor | oxygen concentration in mixing cavity |
|---|---|---|---|---|---|---|---|---|---|---|---|
| Step | FIO2 | Step | FIO2 | Step | FIO2 | Step | FIO2 | Step | FIO2 | Step | FIO2 |
| 1 | 99.52 | 26 | 87.03 | 51 | 73.62 | 76 | 59.73 | 101 | 45.87 | 126 | 32.54 |
| 2 | 99.05 | 27 | 86.51 | 52 | 73.07 | 77 | 59.17 | 102 | 45.33 | 127 | 32.02 |
| 3 | 98.57 | 28 | 85.99 | 53 | 72.52 | 78 | 58.62 | 103 | 44.78 | 128 | 31.51 |
| 4 | 98.09 | 29 | 85.47 | 54 | 71.97 | 79 | 58.06 | 104 | 44.23 | 129 | 31 |
| 5 | 97.6 | 30 | 84.94 | 55 | 71.42 | 80 | 57.5 | 105 | 43.69 | 130 | 30.49 |
| 6 | 97.12 | 31 | 84.41 | 56 | 70.87 | 81 | 56.94 | 106 | 43.15 | 131 | 29.98 |
| 7 | 96.63 | 32 | 83.88 | 57 | 70.31 | 82 | 56.38 | 107 | 42.61 | 132 | 29.47 |
| 8 | 96.14 | 33 | 83.35 | 58 | 69.76 | 83 | 55.83 | 108 | 42.07 | 133 | 28.96 |
| 9 | 95.65 | 34 | 82.82 | 59 | 69.21 | 84 | 55.27 | 109 | 41.53 | 134 | 28.46 |
| 10 | 95.16 | 35 | 82.29 | 60 | 68.65 | 85 | 54.71 | 110 | 40.99 | 135 | 27.96 |
| 11 | 94.66 | 36 | 81.76 | 61 | 68.1 | 86 | 54.16 | 111 | 40.45 | 136 | 27.46 |
| 12 | 94.17 | 37 | 81.22 | 62 | 67.54 | 87 | 53.6 | 112 | 39.91 | 137 | 26.96 |
| 13 | 93.67 | 38 | 80.69 | 63 | 66.98 | 88 | 53.04 | 113 | 39.38 | 138 | 26.46 |
| 14 | 93.17 | 39 | 80.15 | 64 | 66.43 | 89 | 52.49 | 114 | 38.84 | 139 | 25.97 |
| 15 | 92.67 | 40 | 79.61 | 65 | 65.87 | 90 | 51.93 | 115 | 38.31 | 140 | 25.47 |
| 16 | 92.16 | 41 | 79.07 | 66 | 65.31 | 91 | 51.38 | 116 | 37.78 | 141 | 24.98 |
| 17 | 91.66 | 42 | 78.53 | 67 | 64.76 | 92 | 50.38 | 117 | 37.25 | 142 | 24.49 |
| 18 | 91.15 | 43 | 77.99 | 68 | 64.2 | 93 | 50.27 | 118 | 36.72 | 143 | 24 |
| 19 | 90.64 | 44 | 77.45 | 69 | 63.64 | 94 | 49.72 | 119 | 36.19 | 144 | 23.52 |
| 20 | 90.13 | 45 | 76.9 | 70 | 63.08 | 95 | 49.17 | 120 | 35.67 | 145 | 23.03 |
| 21 | 89.62 | 46 | 76.36 | 71 | 62.52 | 96 | 48.62 | 121 | 35.14 | 146 | 22.55 |
| 22 | 89.11 | 47 | 75.81 | 72 | 61.97 | 97 | 48.07 | 122 | 34.62 | 147 | 22.07 |
| 23 | 88.59 | 48 | 75.27 | 73 | 61.41 | 98 | 47.52 | 123 | 34.1 | 148 | 21.6 |
| 24 | 88.07 | 49 | 74.72 | 74 | 60.85 | 99 | 46.97 | 124 | 33.58 | 149 | 21.12 |
| 25 | 87.55 | 50 | 74.17 | 75 | 60.29 | 100 | 46.42 | 125 | 33.06 | 150 | 21 |

OXYGEN MIXING VALVE

FILED OF THE INVENTION

The present invention relates to the field of medical instruments, and more particularly to an oxygen mixing valve.

BACKGROUND OF THE INVENTION

Mechanical ventilation may be performed on a patient during the operation of a medical instrument such as a ventilator or an anesthetic machine. For a patient under treatment, especially an infant patient and a seriously ill patient, it is important to control a ventilation volume and adjust an oxygen concentration. The precision and the grade of the ventilator depend on the precision, sensitivity and continuous adjustment of an oxygen concentration with respect to both a large tidal volume of the adult and a small tidal volume of the infant.

The tidal volume generally refers to the amount of air inhaled or expired during each human breath in a resting state (i.e. a state without stimulation), and depends on age, gender, volume surface, breathing habit and metabolism of the body. The preset tidal volume generally refers to the amount of the inhaled air. The preset tidal volume, which is not constant, is adjustable according to the blood gas analysis of the patient, and normally is: 8-10 ml/kg for an adult and 10-15 ml/kg for an infant.

Presently, the conventional oxygen mixing valve is generally designed so that the mixed proportion of the air and the oxygen is controlled by two flow proportional control valves or end-face seal valves. In the first design of such two designs, two flow proportional control valves are adopted, thus the product manufacturing cost is increased, and it is very difficult for the first design to precisely control the precision of the small tidal volume of the infant. The second one of such two designs adopts two end-face seal valves which are demanding for the precision of manufacturing and assembling of parts, thus the manufacture becomes difficult and the sealing is not good, resulting in an unstable mixed proportional relation of the air and the oxygen.

Figure 1:
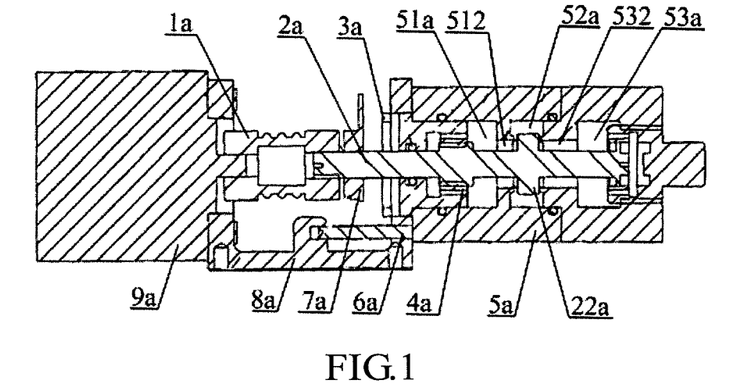
FIG. 1 is a schematic structural diagram of an existing oxygen mixing valve.
Figure 2:
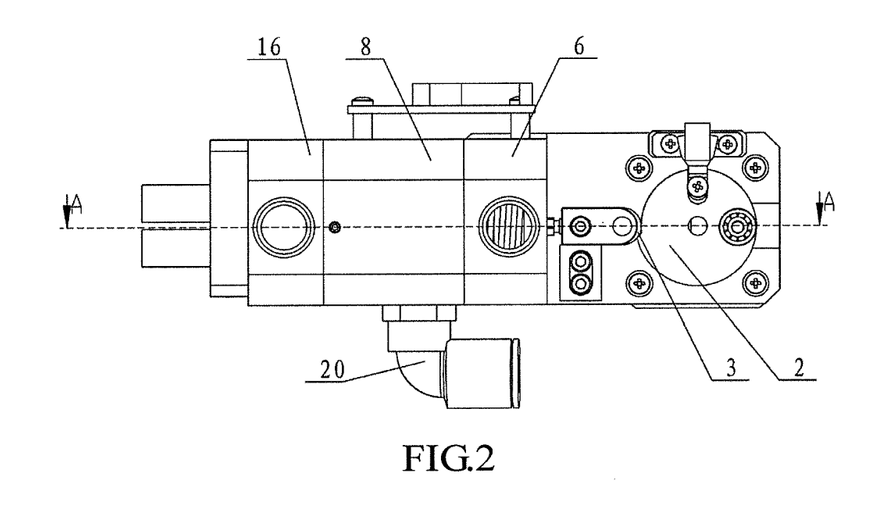
FIG. 2 is a schematic top view of an oxygen mixing valve according to the present invention.
Figure 3:
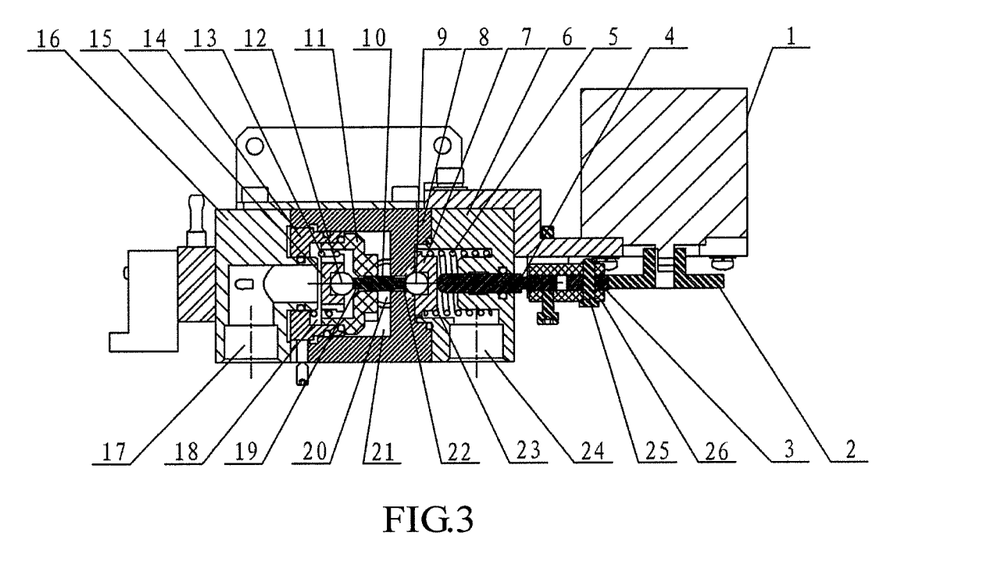
FIG. 3 is a schematic view taken along a line A-A of FIG. 2.
Figure 4:
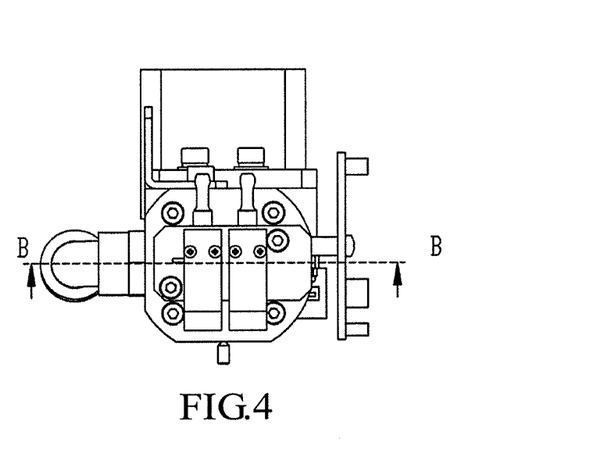
FIG. 4 is a schematic side view of the oxygen mixing valve according to the present invention.
Figure 5:
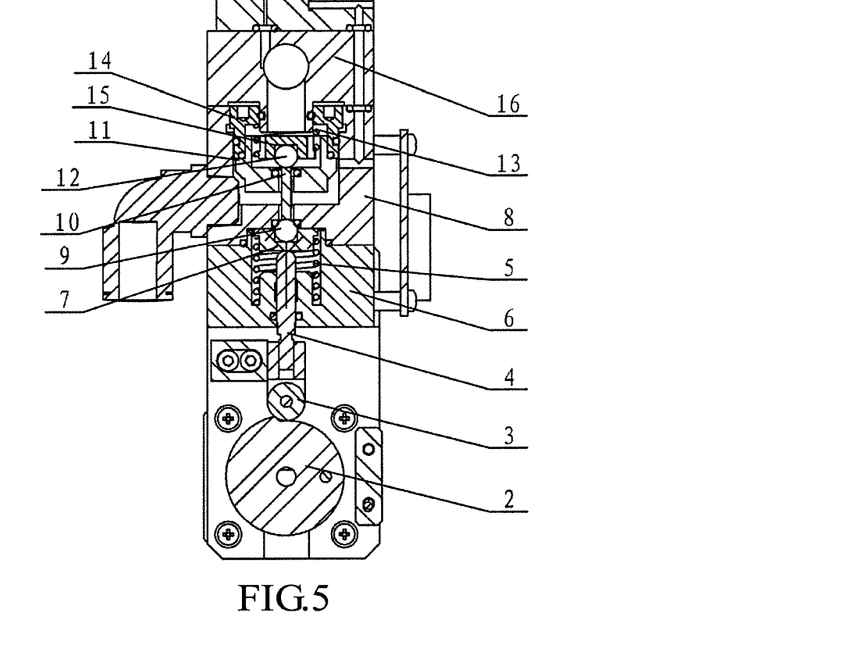
FIG. 5 is a schematic view taken along a line B-B of FIG. 4.

As shown in FIG. 1, Chinese patent No. CN101766861A discloses an air mixing module and a ventilator and an anesthetic machine with the same, in which the air mixing module includes a housing 5a which has a mixing cavity 52a and a first cavity 51a and a second cavity 53a arranged at both sides of the mixing cavity 52a, the first cavity 51a and the second cavity 53a are in communication with the mixing cavity 52a through a first gas outlet 512 and a second gas outlet 532, respectively, a core shaft 2a passes through the first cavity 51a, the mixing cavity 52a and the second cavity 53a in sequence along the axial direction and has a shoulder 22a received in the mixing cavity 52a; furthermore, the air mixing module further includes a step motor 9a used to drive the core shaft 2a to move in the axial direction, thereby simultaneously changing the opening degrees of the first gas outlet 512 and the second gas outlet 532 through the axial movement of the shoulder 22a.

The above solution adopts the step motor 9a for controlling the core shaft 2a to both rotate and displace, through transmission in the form of trapezoidal thread transmission and a gas mixing mechanism kinematic pair in the form of a fixing nut 4a. The core shaft 2a of the gas mixing mechanism is connected with the shaft of the step motor 9a through an elastic coupling 1a, of which the torsional rigidity is sufficient for converting a helical motion into a linear motion, the position of the shaft of the motor can be determined by an opposite-type photoelectric switch 3a, a limit thread 6a and a photoelectric stop plate 7a, etc., and the step motor 9a and the core shaft 2a are positioned by a one-piece bracket 8a, two coaxial holes of which ensure the coaxiality of the motor shaft and the core shaft 2a. An air-oxygen mixing mechanism, which is arranged following an air-inlet module, forms a part of an interior air path of the ventilator before an air intake tube of the ventilator; the air and the oxygen from external gas sources pass through the air-oxygen mixing mechanism, the position of the core shaft 2a within the cavity is precisely controlled by the step motor 9a and the coupling to simultaneously adjust the flows of air and oxygen to achieve the oxygen concentration needed by the patent, and then the tidal of a volume needed by the patent is outputted by a flow proportional valve to an air-intake pipeline.

The disadvantages of the above solution lie in that: firstly, the seal effect is not good enough since the air outlet and oxygen outlet are sealed by only the end-face seal through the shoulder 22a of the core shaft 2a; secondly, such end-face seal is demanding for the flatness of the contact surfaces, thus the manufacture becomes difficult; and thirdly, it is difficult to align the center of the core shaft 2a with that of the motor shaft, such that the core shaft 2a is easily not concentric with the motor shaft, causing the poor seal between the shoulder 22a and the first gas outlet 512 or the second gas outlet 532, as a result, gas leakage is caused and the gas proportions are out of the required ranges.

SUMMARY OF THE INVENTION

An object of the present invention is to solve the problems of high product costs, the poor sealing, the difficult production and manufacture, and the inaccurate control on the oxygen mixing proportion, and provide an oxygen mixing valve, which is advantageous for its small volume, simple structure, convenient installation and maintenance, low manufacture cost, steady and precise adjustment and control on an oxygen concentrate at high pressure, and sensitive and accurate adjustment and control on the oxygen mixing proportion. With an accompanying ordinary proportional valve, the inventive oxygen mixing valve can implement the control for a large or small tidal volume.

The above object of the present invention may be realized by the following technical solution.

An oxygen mixing valve includes a valve body having an oxygen inlet, an air inlet and a mixed-gas outlet, a mixing cavity in communication with the mixed-gas outlet, an oxygen cavity in communication with the oxygen inlet, and an air cavity in communication with the air inlet being arranged in the valve body, characterized in that, a first guide holder is elastically arranged in the oxygen cavity, a second guide holder is elastically arranged in the air cavity, a first ball and a second ball which are connected with a ball driving stem are respectively arranged on inner sides of the first guide holder and the second guide holder, a driving stem is arranged movably on an outer side of the first guide holder, a rotatable bearing is arranged on an outer end of the driving stem, and an involute cam connected with an output shaft of a step motor is arranged on an outer end of the bearing, thus the rotation of the output shaft of the step motor causes the rotation of the involute cam, which further drives the bearing to rotate and displace horizontally to push the driving stem to move in the axial direction, thereby adjusting an opening degree of the outlet of the air cavity and that of the oxygen cavity.

Preferably, the valve body includes a first valve body, a second valve body and a third valve body arranged successively, the mixing cavity containing a first valve core body and a second valve core body is arranged in the second valve body, the first valve core body and the second valve core body are connected to communicate with each other and form an air cavity interiorly, the oxygen cavity is arranged in the first valve body, the air cavity is in communication with the mixing cavity through an air outlet arranged on the first valve core body, and the oxygen cavity is in communication with the mixing cavity through an oxygen outlet arranged on the second valve body.

Preferably, the outer side of the first guide holder is connected with the first valve body by a first spring, the outer side of the second guide holder is connected with the third valve body by a second spring, the air inlet is arranged on the third valve body and is in communication with the air cavity arranged within the second valve body, and the oxygen inlet is arranged on the first valve body and is in communication with the oxygen cavity arranged within the first valve body.

Preferably, two splints placed one above the other are fixedly arranged at one side of the valve body, the bearing is arranged between the two splints, and a pin extends through the splints and the bearing to connect them together, the driving stem is arranged within the first valve body, one end of the driving stem extends into the oxygen cavity to abut against the outer side of the first guide holder, and the other end of the driving stem extends between the two splints.

Further, one end of the air outlet is provided with a tapered face mated with the second ball, one end of the oxygen outlet is provided with a tapered face mated with the first ball, so that a reliable sealing can be formed and an accurate control on the ventilation volume can be realized by the fit between the tapered face and the ball, the ball driving stem is arranged in the mixing cavity, and two ends of the ball driving stem respectively extend into the air outlet and the oxygen outlet.

Further, an axis of the driving stem, a center of the first ball, an axis of the ball driving stem and a center of the second ball are on the same line, this design can ensure the accurate control on the mixing proportion of the air and the oxygen.

Further, an elastic force of the second spring is greater than that of the first spring, such that the second ball always blocks the air outlet and hence the air outlet end is in a closed state, and the first ball is away from the oxygen outlet and hence the oxygen outlet end is in an entirely open state, under the normal condition.

Preferably, an O-shaped sealing ring is arranged on each of a contact face between the first valve body and the second valve body, a contact face between the second valve body and the second valve core body, a contact face between the second valve core body and the third valve body, and a contact face between the second valve core body and the first valve core body.

Preferably, an O-shape sealing ring is arranged on the contact face between the driving stem and the first valve body.

Preferably, a sealing diaphragm is arranged on the contact face between the driving stem and the first valve body.

The present invention is advantageous as follows. The step motor is used to rotate the involute cam, which in turn drives the bearing to rotate and horizontally displace simultaneously to push and move the driving stem, so that the reliable sealing can be formed between the ball and the tapered face of the valve body and the accurate control on the ventilation volume can be realized. Further, in the case of different flows, the rotational angle of the step motor can be linearly converted into a change of the gas flow, which provides a good mechanical structure platform for achieving automation control. The sealing of the valve is safe and cost effective and is convenient in disassembly and maintenance, because of the O-shaped sealing ring used in each sealed portion in the oxygen mixing valve. Since the axis of the driving stem, the center of the first ball, the axis of the ball driving stem and the center of the second ball lie on the same line, the first ball and the second ball can be used for opening proportionately the respective outlet, thereby ensuring a high precision of the oxygen mixing valve. With the springs arranged in the oxygen mixing valve, the first guide holder and the second holder can be pre-pressed; further, the prepressing force of the second spring is greater than that of the first spring, thus ensuring that the driving stem is pressed closely on the balls at its two sides, as a result, under the normal condition, the second ball always blocks the air outlet and hence the air outlet is in the closed state; while the first ball is away from the oxygen outlet and hence the oxygen outlet is in the entirely open state. In view of the prior art, the inventive oxygen mixing valve is advantageous for its small volume, simple structure, convenient installation and maintenance, low manufacture cost, steady and precise adjustment and control on an oxygen concentrate at high pressure, and sensitive and accurate adjustment and control on the oxygen mixing proportion. With an accompanying ordinary proportional valve, the inventive oxygen mixing valve can implement the control for a large or small tidal volume.

BRIEF DESCRIPTION OF THE DRAWINGS

The present invention will be further described in detail below according to the accompanying drawings and embodiments.

FIG. 10 shows a table including the number of steps made by the step motor and the mixed oxygen concentration calculated by the formula;

REFERENCE NUMERAL LIST

| 1a: elastic coupling | 2a: core shaft | 3a: photoelectric switch |
| --- | --- | --- |
| 4a: fixing nut | 5a: housing | 6a: limit thread |

| | | |
|---|---|---|
| 7a: photoelectric stop plate | 8a: bracket | 9a: step motor |
| 22a: shoulder | 51a: first cavity | 52a: mixing cavity |
| 53a: second cavity | 512: first gas outlet | 532: second gas outlet |
| 1: step motor | 2: involute cam | 3: bearing |
| 4: driving stem | 5: first spring | 6: first valve body |
| 7: first guide holder | 8: second valve body | 9: first ball |
| 10: ball driving stem | 11: first valve core body | 12: second ball |
| 13: second spring | 14: second valve core body | 15: second guide holder |
| 16: third valve body | 17: air inlet | 18: air cavity |
| 19: air outlet | 20: mixed-gas outlet | 21: mixing cavity |
| 22: oxygen outlet | 23: oxygen cavity | 24: oxygen inlet |
| 25: pin | 26: splint | |

DETAILED DESCRIPTION OF THE EMBODIMENTS

In the embodiment shown in FIGS. 2 to 6, an oxygen mixing valve according to the present invention includes a valve body having an oxygen inlet 24, an air inlet 17 and a mixed-gas outlet 20. A mixing cavity 21 in communication with the mixed-gas outlet 20, an oxygen cavity 23 in communication with the oxygen inlet 24, and an air cavity 18 in communication with the air inlet 17 are arranged in the valve body. A first guide holder 7 is elastically arranged in the oxygen cavity 23, a second guide holder 15 is elastically arranged in the air cavity 18, a first ball 9 and a second ball 12 which are contacted with a ball driving stem 10 are respectively arranged on inner sides of the first guide holder 7 and the second guide holder 15, a driving stem 4 is arranged movably on an outer side of the first guide holder 7, a rotatable bearing 3 is arranged on an outer end of the driving stem 4, and an involute cam 2 connected with an output shaft of a step motor 1 is arranged on an outer end of the bearing 3, thus the rotation of the output shaft of the step motor 1 causes the rotation of the involute cam 2, which further drives the bearing 3 to rotate and displace horizontally to push the driving stem 4 to move in the axial direction, thereby adjusting an opening degree of the outlet of the air cavity 18 and that of the oxygen cavity 23.

The oxygen mixing valve as shown in FIGS. 2 to 5 includes a first valve body 6, a second valve body 8 and a third valve body 16 arranged successively from right to left, the oxygen inlet 24 arranged on the first valve body 6 is in communication with the oxygen cavity 23 arranged within the first valve body 6. Furthermore, the second valve body 8 contains the mixing cavity 21, in which a first valve core body 11 and a second valve core body 14 are also disposed. The first valve core body 11 and the second valve core body 14 are arranged oppositely and connected with each other to form an air cavity 18 therebetween. Also, the air inlet 17 in communication with the air cavity 18 is arranged on the third valve body 16, an air outlet 19 is arranged on the first valve core body 11 and an oxygen outlet 22 is arranged on the second valve core body 14, the air cavity 18 is in communication with the mixing cavity 21 through an air outlet 19, and the oxygen cavity 23 is in communication with the mixing cavity 21 through the oxygen outlet 22.

The first guide holder 7 is connected with the first valve body 6 at its outer side by a first spring 5, and provided with a groove at its inner side, so that the first ball 9 is installed within the groove. The second guide holder 15 in connected with the third valve body 16 at its outer side by a second spring 13, and provided with a groove at its inner side, so that the second ball 12 is installed within the groove at the inner side. The ball driving stem 10 is arranged between the first ball 9 and the second ball 12, and the centers of the ball driving stem 10, the first ball 9 and the second ball 12 lie on the same line. The ball driving stem 10 lies in the mixing cavity 21, one end of the ball driving tem 10 extends into the oxygen outlet 22 and the other end extends into the air outlet 19, and the elastic forces of the first spring 5 and the second spring 13 drives the first ball 9, the ball driving stem 10 and the second ball 12 to abut together. The end of the oxygen outlet 22 that corresponds to the first ball 9 is designed to have a tapered face to mate with the first ball 9, and the end of the air outlet 19 that corresponds to the second ball 12 is designed to have a tapered face to mate with the second ball 12. At the outside of the first valve body 6, two splints 26 placed one above the other are fixedly arranged on the valve body, the bearing 3 is arranged between the two splints 26 which constitute a bearing seat, a pin 25 extends through the bearing 3 and the two splints 26 to connect them together, such that the bearings 3 can be rotated around the pin 25. The driving stem 4 is arranged within the first valve body 6, one end of the driving stem 2 extends into the oxygen cavity 23 to abut against the outer side of the first guide holder 7, and the other end extends between the two splints 26 and is threadedly connected to the splints. When the bearing 3 is rotated and horizontally displaced, the splint and the driving stem are axially moved, thus the linkage of the first guide holder 7, the first ball 9, the ball driving stem 10 and the second ball 12 can be achieved, to adjust the opening degrees of the air outlet 19 and the oxygen outlet 22. In order to ensure the reliability of the movement, the axis of the driving stem 4, the center of the first ball 9, the axis of the ball driving stem 10 and the center of the second ball 12 are designed to lie on the same line.

In order to press the ball driving stem 10 closely together with the balls at its two ends, the elastic force of the second spring 13 is larger than that of the first spring 5, as a result, under the normal condition (i.e. when the step motor does not work), the second ball 12 closes the air outlet 19 under the action of the elastic force of the second spring 13 and the air outlet end is in the closed state, while the first ball 9 is away from the oxygen outlet 22 under the action of the elastic force of the second spring 13 and the oxygen outlet end is in the entirely open state.

In order to improve the sealing performance of the oxygen mixing valve, an O-shaped sealing ring is arranged for sealing at each of the contact face between the driving stem 4 and the first valve body 6, the contact face between the first valve body 6 and the second valve body 8, the contact face between the second valve body 8 and the second valve core body 14, the contact face between the second valve core body 14 and the third valve body 16 as well as the contact face between the second valve core body 14 and the first valve core body 11. Such a sealing manner can not only save costs but also facilitate the disassembly and maintenance of the oxygen mixing valve.

However, the long-term relative motion of the driving stem 4 relative to the first valve body 6 may easily lead to the wear of the O-shaped sealing ring on the contact surface between the driving stem 4 and the first valve body 6, thus periodic replacement of the O-shaped sealing ring is necessary. Therefore, in order to ensure the better sealing performance and avoid the periodic replacement of the O-shaped sealing ring, a sealing diaphragm may be employed on the contact face between the driving stem 4 and the first valve body 6.

Figure 6:
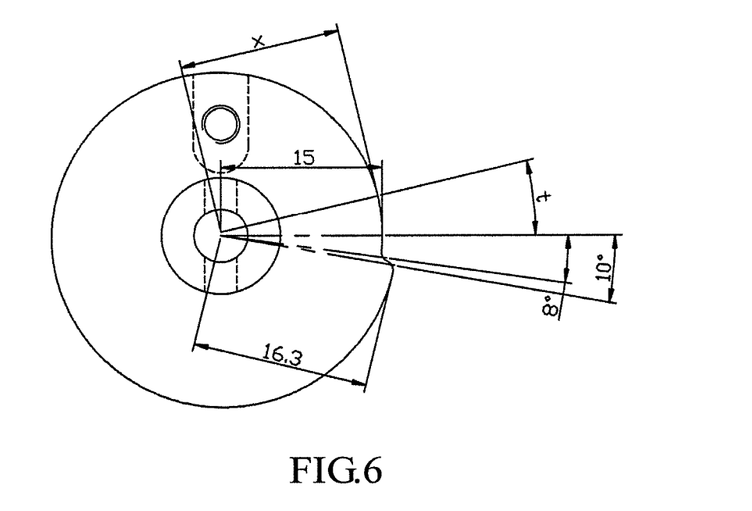
FIG. 6 is a schematic structural view of an involute cam of the oxygen mixing valve according to the present invention.

In order to accurately control the ventilation volume of the oxygen mixing valve, the outer contour of the cam in the oxygen mixing valve is designed in an involute form, here, the initial angle of the involute is 0°, and the end angle in the counterclockwise direction is 350°. As shown in FIG. 6, an arc with a radius of 15 mm is formed in a labeled angle of 8° starting from the initial angle in the clockwise direction. The maximum displacement of 1.2 mm of the driving stem 4 is caused when the involute cam 2 is rotated by 324°, in this way, the displacement X of the driving stem 4 may be calculated by a formula of X=15+(t/350°)×1.3, where t represents the rotation angle of the cam. Numerous verifications show that the operation angle of the involute cam 2 is preferably 270°, that is, the oxygen concentration will be decreased from 100% to 21% when 0 to 150 steps are made by the motor (1.8°/per step). When the involute cam 2 is rotated by 270°, the distance of the horizontal displacement of the driving stem 4 is: 270/350×1.3=10 mm, and if a step of 1.8° (i.e. one operation step) is made by the motor, the displacement distance of the ball is: 1.8/350×1.3=0.0067 mm. In order to ensure the normal operation and easy calculation, the distance of the above horizontal displacement from the state where oxygen is blocked to the state where air is blocked is 1 mm in the oxygen mixing valve.

Figure 7:
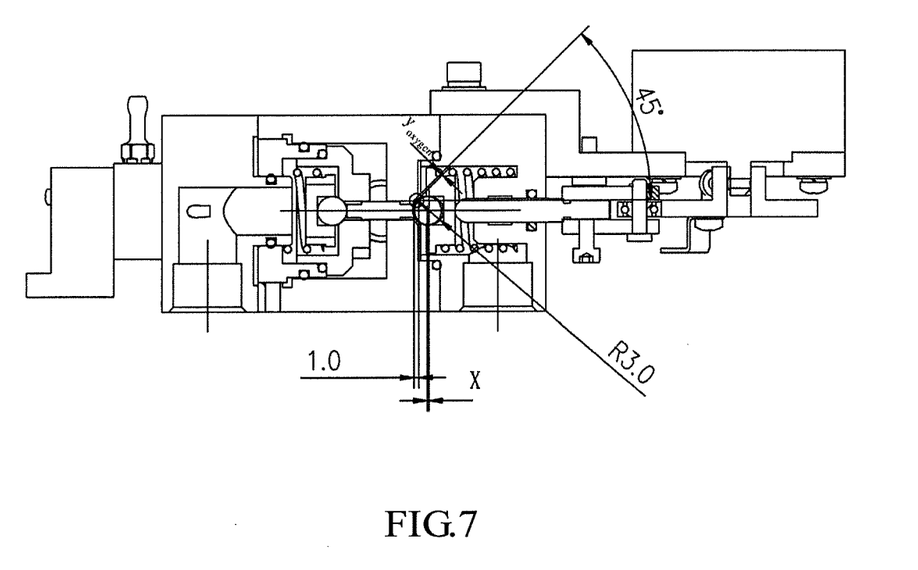
FIG. 7 is a schematic diagram showing the state with the maximum flow of oxygen in the oxygen mixing valve according to the present invention.
Figure 8:
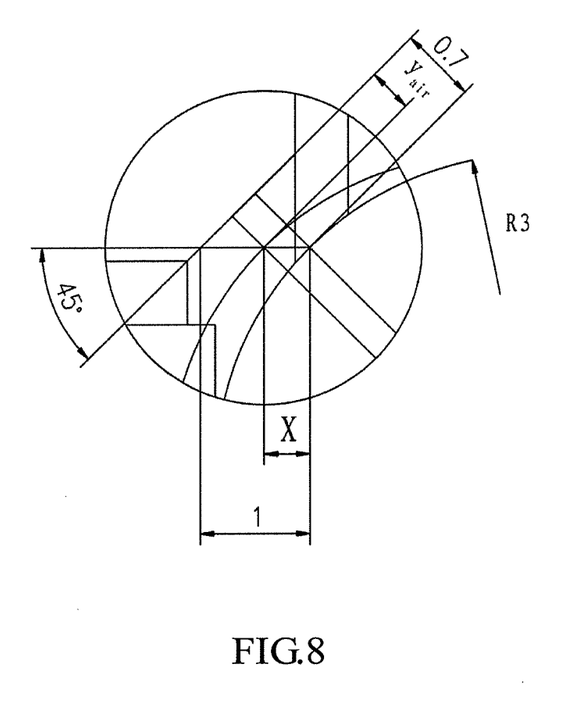
FIG. 8 is a diagram showing an operation state of the ball at the air outlet end and the tapered face in the oxygen mixing valve according to the present invention.
Figure 9:
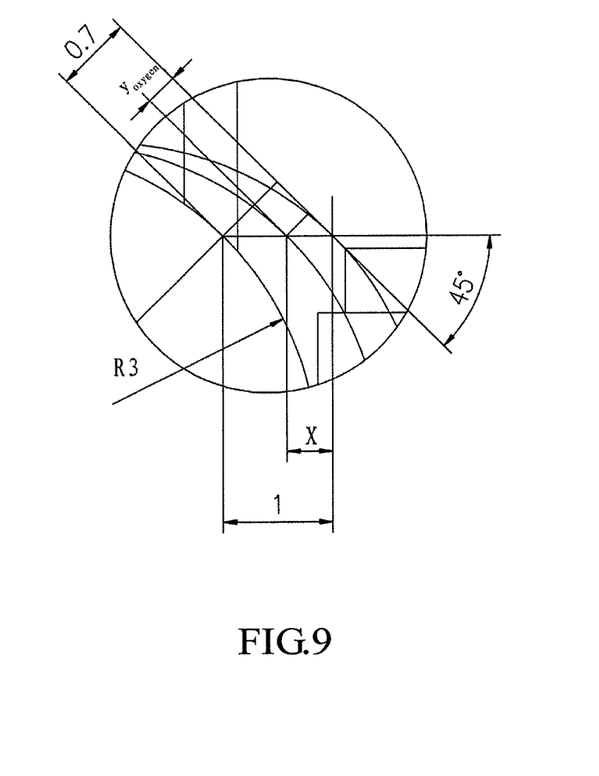
FIG. 9 is a diagram showing an operation state of the ball at the oxygen outlet end and the tapered face in the oxygen mixing valve according to the present invention.

As shown in FIGS. 7 to 9, the functional relationship between the oxygen concentration and the displacement amount of the driving stem 7 is as follows:

$$y_{oxygen}=0.7x, y_{air}=0.7(1-x),$$

$$s_{oxygen}=3.14\{(y_{oxygen}+3)^2-9\}=3.14\{(0.7x+3)^2-9\},$$

$$s_{air}=3.14\{(y_{air}+3)^2-9\}=3.14\{(3.7-0.7x)^2-9\},$$

the oxygen flow passing through the oxygen mixing valve in unit time=(flow rate×$s_{oxygen}$)+(flow rate×$s_{air}$×21%), the functional relationship between the mixed-oxygen concentration $O_2$% and x is as follows: the mixed-oxygen concentration $O_2$%={(flow rate×$s_{oxygen}$)+(flow rate×$s_{air}$×21%)}/{(flow rate×$s_{oxygen}$)+(flow rate×$s_{air}$)}×100%, which may be simplified as:

the mixed-oxygen concentration $O_2$%=($s_{oxygen}$+$s_{air}$×21%)/($s_{oxygen}$+$s_{air}$)×100%, the functional relationship between the motor steps and the mixed oxygen concentration is as follows:

the number of steps made by the motor T=(1−x)/0.007, the mixed-oxygen concentration $O_2$%=[($s_{oxygen}$+$s_{air}$×21%)/($s_{oxygen}$+$s_{air}$)]×100%=[3.14{(0.7x+3)−9}+3.14{(3.7−0.7x)−9}×21%]/[3.14{(0.7x+3)−9}+3.14{(3.7−0.7x)−9}]×100% =[0.5928x+3.1122x+0.9849]/[0.98x−0.98x+4.69]×100%, where, $y_{oxygen}$ denotes the distance between the first ball 9 and the corresponding tapered face, $y_{air}$ denotes the distance between the second ball 12 and the corresponding tapered face, x denotes the distance of the horizontal displacement of the ball, $s_{oxygen}$ denotes the sectional area for oxygen ventilation corresponding to the ball distance x, and $s_{air}$ denotes the sectional area for air ventilation corresponding to the ball distance x.

Figure 11:
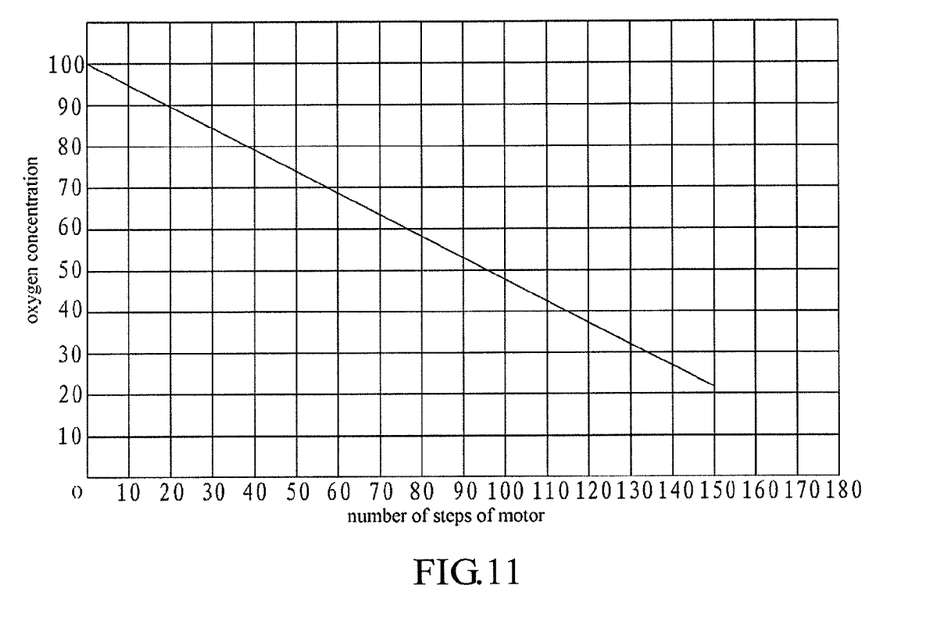
FIG. 11 is a graph of the number of steps made by the step motor versus the oxygen concentration obtained according to the data calculated by the formula.

According to the above functional relationship, a table and a graph of the number of steps made by the step motor and the mixed oxygen concentration can be obtained (as shown in FIGS. 10 and 11). It can be seen from the table and the graph that, in a certain displacement range of the ball, the ventilation volume is in an approximate linear relationship with the displacement distance of the ball, thus the automatic control can be achieved conveniently.

Figure 12:
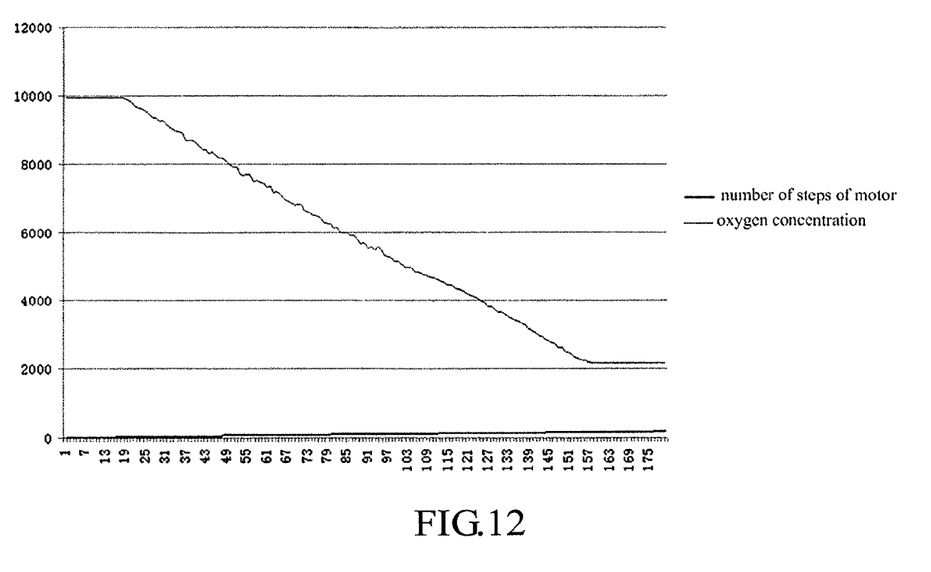
FIG. 12 is a graph of the number of steps of the step motor versus the oxygen concentration obtained according to the actual experimental data.

Ten manufactured, assembled and calibrated oxygen mixing valves are tested on the test equipment, to obtain the graph of the number of steps made by the step motor versus the mixed oxygen concentration (as shown in FIG. 12). It can be seen from the graph that the tested graph is extremely close to the calculated graph. Of course, in practice, a certain margin is kept at the air end and the oxygen end of the oxygen mixing valve when air and oxygen is closed for the sake of adjustment and calibrating.

The operation steps of the oxygen mixing valve are as follows. Before the use of the oxygen mixing valve, it is determined whether the involute cam 2 has been reset to the lowest position, i.e. a state with the maximum oxygen flow and without air flow. Then the initial position of the involute cam 2 is calibrated using a photoelectric sensor and the step motor 1 is started. Next, the number of steps to be made by the step motor 1 is adjusted according to the required oxygen concentration, then the step motor 1 drives the involute cam 2 to rotate by the corresponding angle, such that the involute cam 2 drives the bearing 3 to be rotated and displaced by a certain distance, the bearing 3 in turn pushes the driving stem 4 to be displaced by a corresponding distance in the horizontal direction, further, the driving stem 4 pushes the first guide holder 7 and the first ball 9 to displace left by a certain distance, and the first ball 9 in turn pushes the ball driving stem so that the second ball 12 is moved away from the air outlet, at this time, the air passes through the air outlet 19 from the air cavity 18 into the mixing cavity 21, thereby reducing the oxygen concentration in the mixing cavity 21 to the required oxygen concentration. After the use, it is preferable to determine whether the involute cam 2 has been reset to the lowest position, i.e. the state with the maximum oxygen flow and without air flow, and then the power is turned off.

The inventive oxygen mixing valve overcomes the instability of the oxygen mixing mechanism used at high pressure, accurately controls the oxygen concentration in a relatively large flow range, and has an improved seal effect. If a pair of pressure-reducing valves are mounted preceding to the oxygen mixing mechanism, a pressure difference between the output air and the output oxygen can be kept below 0.03 KPa for the case of different pressure of the input air and the input oxygen (but the pressure of the input air and oxygen should be no more than 600 KPa), in this way, the accurate control on the mixed proportion can be achieved with the oxygen mixing valve, while the continuous adjustment to the oxygen concentration can be achieved for a range from a large tidal volume of the adult to a small tidal volume of the infant.

What is claimed is:

1. An oxygen mixing valve, comprising a valve body having an oxygen inlet, an air inlet and a mixed-gas outlet, a mixing cavity in communication with the mixed-gas outlet, an oxygen cavity in communication with the oxygen inlet, and an air cavity in communication with the air inlet being arranged in the valve body, wherein, a first guide holder is arranged in the oxygen cavity, a second guide holder is arranged in the air cavity, a first ball and a second ball which are connected with a ball driving stem are respectively arranged on an inner sides of the first guide holder and an inner side of the second guide holder, a driving stem is arranged movably on an outer side of the first guide holder, a rotatable bearing is arranged on an outer end of the driving stem, and an involute cam connected with an output shaft of a step motor is arranged on an outer end of the bearing, wherein the inner side of the first guide holder is a concave side of the first guide holder, the outer side of the first guide holder is a side opposite to the concave side of the first guide holder, the inner side of the second guide holder is a concave side of the second guide holder, the outer side of the second guide holder is a side opposite to the concave side of the second guide holder, and the outer end of the driving stem is an end closer to the mixing cavity than an inner end of the driving stem, and wherein, the valve body includes a first valve body, a second valve body and a third valve body arranged successively, the mixing cavity containing a first valve core body and a second valve core body is arranged in the second valve body, the first valve core body and the second valve core body are connected to communicate with each other and form an air cavity interiorly, the oxygen cavity is arranged in the first valve body, the air cavity is in communication with the mixing cavity through an air outlet arranged on the first valve core body, and the oxygen cavity is in communication with the mixing cavity through an oxygen outlet arranged on the second valve body.

2. The oxygen mixing valve of claim 1, wherein, the outer side of the first guide holder is connected with the first valve body by a first spring, the outer side of the second guide holder is connected with the third valve body by a second spring, the air inlet is arranged on the third valve body and is in communication with the air cavity arranged within the second valve body, and the oxygen inlet is arranged on the first valve body and is in communication with the oxygen cavity arranged within the first valve body.

3. The oxygen mixing valve of claim 2, wherein, an elastic force of the second spring is greater than that of the first spring, such that the oxygen outlet end is in an entirely open state and the air outlet is in a closed state under the normal condition.

4. The oxygen mixing valve of claim 3 wherein, an O-shaped sealing ring is arranged on each of a contact face between the first valve body and the second valve body, a contact face between the second valve body and the second valve core body, a contact face between the second valve core body and the third valve body, and a contact face between the second valve core body and the first valve core body.

5. The oxygen mixing valve of claim 2 wherein, an O-shaped sealing ring is arranged on each of a contact face between the first valve body and the second valve body, a contact face between the second valve body and the second valve core body, a contact face between the second valve core body and the third valve body, and a contact face between the second valve core body and the first valve core body.

6. The oxygen mixing valve of claim 1, wherein, two splints placed one above the other are fixedly arranged at one side of the valve body, the bearing is arranged between the two splints, and a pin extends through the splints and the bearing to connect them together, the driving stem is arranged within the first valve body, one end of the driving stem extends into the oxygen cavity to abut against the outer side of the first guide holder, and the other end of the driving stem extends between the two splints.

7. The oxygen mixing valve of claim 6, wherein, an O-shaped sealing ring is arranged on a contact face between the driving stem and the first valve body.

8. The oxygen mixing valve of claim 6, wherein, a sealing diaphragm is arranged on the contact face between the driving stem and the first valve body.

9. The oxygen mixing valve of claim 1, wherein, one end of the air outlet is provided with a tapered face mated with the second ball, one end of the oxygen outlet is provided with a tapered face mated with the first ball, the ball driving stem is arranged in the mixing cavity, and two ends of the ball driving stem respectively extend into the air outlet and the oxygen outlet.

10. The oxygen mixing valve of claim 9 wherein, an O-shaped sealing ring is arranged on each of a contact face between the first valve body and the second valve body, a contact face between the second valve body and the second valve core body, a contact face between the second valve core body and the third valve body, and a contact face between the second valve core body and the first valve core body.

11. The oxygen mixing valve of claim 1, wherein, an axis of the driving stem, a center of the first ball, an axis of the ball driving stem and a center of the second ball are on the same line.

12. The oxygen mixing valve of claim 11 wherein, an O-shaped sealing ring is arranged on each of a contact face between the first valve body and the second valve body, a contact face between the second valve body and the second valve core body, a contact face between the second valve core body and the third valve body, and a contact face between the second valve core body and the first valve core body.

13. The oxygen mixing valve of claim 1 wherein, an O-shaped sealing ring is arranged on each of a contact face between the first valve body and the second valve body, a contact face between the second valve body and the second valve core body, a contact face between the second valve core body and the third valve body, and a contact face between the second valve core body and the first valve core body.

* * * * *